United States Patent [19]

von Werner et al.

[11] 4,400,325

[45] Aug. 23, 1983

[54] PROCESS FOR THE PREPARATION OF PURE, SATURATED PERFLUOROALKANE-1-CARBOXYLIC ACIDS FROM 1-IODOPERFLUOROALKANES

[75] Inventors: Konrad von Werner; Alfons Gisser, both of Burgkirchen, Fed. Rep. of Germany

[73] Assignee: Hoechst Aktiengesellschaft, Fed. Rep. of Germany

[21] Appl. No.: 319,701

[22] Filed: Nov. 9, 1981

[30] Foreign Application Priority Data

Nov. 15, 1980 [DE] Fed. Rep. of Germany ....... 3043249

[51] Int. Cl.$^3$ ............................ C09F 7/00; C11C 3/00
[52] U.S. Cl. .................................. 260/408; 562/541; 562/605
[58] Field of Search ................. 260/408; 562/541, 605

[56] References Cited

U.S. PATENT DOCUMENTS 2,904,567  9/1959  Barnhart .......................... 260/408
3,351,644  11/1967  Hauptschein ..................... 260/408

Primary Examiner—John F. Niebling
Attorney, Agent, or Firm—Connolly & Hutz

[57] ABSTRACT

Saturated perfluoroalkane-1-carboxylic acids having 6 to 14 C atoms are prepared by reacting the corresponding 1-iodoperfluoroalkanes at temperatures of 100° to 180° C. with fuming sulfuric acid containing 15 to 45% by weight of dissolved sulfur trioxide. The two liquid phases which are formed are separated. The lighter phase is mixed with 0.3 to 6% of its weight of water and is distilled at a pressure of 0.3 to 100 kPa. The heavier phase is mixed with 0.7 to 1.5 moles of water per mole of sulfur trioxide employed and is cooled to 0° to +30° C. and the precipitated iodine is filtered off. After the addition of sulfur trioxide, the liquid filtrate can be re-used.

Perfluoroalkan-1-oic acids are obtained in a high state of purity and the bulk of the iodine is recovered in the elementary form.

7 Claims, No Drawings

PROCESS FOR THE PREPARATION OF PURE, SATURATED PERFLUOROALKANE-1-CARBOXYLIC ACIDS FROM 1-IODOPERFLUOROALKANES

The invention relates to a process for the preparation of pure, in particular straight-chain, perfluorocarboxylic acids from 1-iodoperfluoroalkanes, in a high yield. The invention also relates to an effective method for recovering the iodine.

Perfluorocarboxylic acids are non-oxidizing, strong acids which are distinguished by an outstanding stability to heat and chemicals and, as a result of the perfluoroalkyl radical, possess good surface-active properties.

The perfluorinated carboxylic acids are suitable for use as vaporization suppressors with volatile, combustible organic liquids. In the form of their ammonium or alkali metal salts, they are used as emulsifiers, for example in the polymerization of fluorinated alkenes, for example tetrafluoroethylene. In addition, the fluorinated carboxylic acids constitute valuable intermediate products for the preparation of other fluorinated surfactants, in particular oil-repellent and water-repellent agents.

It is known to prepare perfluorocarboxylic acids by hydrolyzing corresponding acid halides, which are accessible from fluorine-free precursors by electrochemical fluorination (Chemiker-Zeitung, Issue No. 1, 1976, page 6). However, this process is not without hazards owing to the use of liquid hydrogen fluoride and, particularly in the case of long-chain carboxylic acids, gives low yields.

Another known process for the preparation of perfluorocarboxylic acids consists in reacting perfluoroalkyl-magnesium halides with carbon dioxide (Journal of the Chemical Society, 1952, page 3,423) or dialkyl carbonates (German Pat. No. 1,926,942). However, a disadvantage here is the thermolability of the fluoroalkyl Grignard compounds, which causes technical difficulties.

It is also known that perfluorocarboxylic acids can be prepared by reacting perfluorohalogenoalkanes with gaseous carbon dioxide and a zinc/metal couple of the formula $ZnM^2$ wherein $M^2$ is a more electropositive metal compared with zinc, using dialkyl sulfoxides as the solvent (German Offenlegungsschriften Nos. 2,708,751 and 2,756,169). A disadvantage of this process of preparation is the poor stability of the dialkyl sulfoxides towards reducing agents. Perfluorocarboxylic acids are, therefore, obtained, to which the foul odor of a dialkyl sulfide adheres, even after purification by distillation. A similar process makes use of substituted carboxylic acid amides as the solvent, whereby adducts of the perfluorocarboxylic acids with the carboxylic acid amides used being formed first, from which the acid has to be liberated in a separate stage (German Offenlegungsschrift No. 2,848,197).

Similarly, it is known that perfluorocarboxylic acids can be prepared by oxidizing perfluoroolefins (Journal of the American Chemical Society, Volume 75, pages 2,698 to 2,702), or perfluoroalkanes containing $CCl_3$, $CFCl_2$ or $CFClBr$ terminal groups (U.S. Patent Nos. 2,806,865 and 2,806,866). However, these processes are expensive and difficult to carry out on an industrial scale.

Furthermore, it is known from German Patent No. 1,211,619 that perfluorocarboxylic acids are obtained, together with the corresponding acid fluorides, in the reaction of 1-iodoperfluoroalkanes with fuming sulfuric acid. The examples indicated in the said patent specification only describe reactions of branched-chain starting compounds. After the reaction with the 1-iodoperfluoroalkane, the fuming sulfuric acid which has been separated off is stated to be re-usable for a further reaction with 1-iodoperfluoroalkane, after adding sulfur trioxide and filtering.

In general, there is a need for processes which make it possible to prepare the perfluorocarboxylic acids having 6 to 14 C atoms, which are valued because of their advantageous properties described earlier in the text. Starting materials which are suitable for this purpose are, in particular, straight-chain 1-iodoperfluoroalkanes of the formula $CF_3(CF_2)_xI$ wherein x denotes an integer from 5 to 13, since such compounds are readily accessible by telomerization of iodotrifluoromethane or iodopentafluoroethane with tetrafluoroethylene.

The object of the present invention is to provide a process which makes it possible to obtain, at a favorable cost efficiency, the said perfluorocarboxylic acids in a good yield and purity and with substantial recovery of the valuable elementary iodine.

This object is achieved by a process for the preparation of pure, saturated perfluoroalkane-1-carboxylic acids having 6 to 14 C atoms from the corresponding 1-iodoperfluoroalkanes, with substantial recovery of iodine, by reacting the 1-iodoperfluoroalkanes with fuming sulfuric acid containing 15 to 45% by weight, relative to the solution, of dissolved sulfur trioxide, at temperatures of 100° to 180° C., if appropriate under pressure, the molar ratio of sulfur trioxide to 1-iodoperfluoroalkane being 2:1 to 15:1 and the resulting two liquid phases being separated from one another when the reaction is complete, which comprises mixing, if appropriate at elevated temperature, the lighter liquid phase with 0.3 to 6% of its weight of water or with a corresponding amount of an aqueous liquid, and then distilling this mixture at a pressure of 0.1 to 100 kPa, and also mixing, if appropriate while additionally heating, the heavier liquid phase, which has been separated off after the reaction with fuming sulfuric acid, with 0.7 to 1.5 moles of water, or with a corresponding amount of an aqueous sulfuric acid, per mole of sulfur trioxide employed, then cooling to 0° to +30° C., filtering off the solid iodine which has been precipitated, washing it with aqueous sulfuric acid and with water and, if appropriate, drying and purifying it by known methods.

The fuming sulfuric acid should contain between 15 and 45% by weight, advantageously between 30 and 40% by weight, of sulfur trioxide. If the sulfur trioxide content is less than 15% by weight, the reaction is too slow, while if the content is above 45% by weight, interfering side reactions take place.

The reaction is carried out at at least 100° C. so that it may take place at a sufficient rate. On the other hand, temperatures above 180° C. should be avoided, in order to prevent side reactions, such as, for example, cracking processes at the perfluoroalkyl chain. It is preferable to work at 130° to 170° C.; the optimum range is between 140° and 160° C.

The molar ratio of the sulfur trioxide employed to 1-iodoperfluoroalkane should be 2:1 to 15:1. If the ratio is less than 2, it is impossible to achieve a sufficient conversion even with very long reaction times, while a ratio greater than 15 is not only associated with the use of an unnecessary quantity of fuming sulfuric acid, but also leads to an impairment of the yield as a result of increasing side reactions. Particularly for the reaction of sulfur trioxide with 1-iodoperfluoroalkanes containing 6 to 14 C atoms, molar ratios of 3:1 to 6:1 are advantageous.

The reaction of the 1-iodoperfluoroalkane with fuming sulfuric acid is best carried out in a closed system, in order to prevent an escape of sulfur trioxide or iodoperfluoroalkane. An example of a suitable reaction vessel is a steel kettle or autoclave. The steel surface is rendered passive under the influence of the sulfur trioxide, both in the liquid phase and in the gas phase. A protective layer which prevents corrosion is formed.

It is advantageous to mix the reactants vigorously during the reaction; this can be achieved by customary methods, for example by stirring or shaking.

Depending on the temperature chosen and the chain length of the 1-iodoperfluoroalkane employed, the reaction is generally complete in about 1 to about 12 hours. At temperatures within the range from 130° to 170° C., the reaction is complete in 4 to 8 hours if the 1-iodoperfluoroalkane has an average chain length. For 1-iodoperfluoroalkanes of longer chain length, it is advisable to prolong the duration of the reaction by 1 to 3 hours.

In most cases, on cooling to about 20° C., the reaction mixture separates smoothly into two phases which can be separated easily owing to their different colors. The light-colored, lighter phase consists essentially of the acid fluoride $CF_3(CF_2)_{x-1}COF$ and of the carboxylic acid $CF_3(CF_2)_{x-1}COOH$ (x has the meaning mentioned above). The dark brown, heavier phase consists mainly of sulfuric acid, sulfur trioxide, fluorosulfonic acid, iodine, hydrogen iodide and sulfur dioxide.

In the preparation of relatively short-chain carboxylic acids, in particular perfluorohexanoic acid, the fluorine products dissolve noticeably in the heavier phase. They can be extracted from the latter with the aid of solvents which are not miscible with fuming sulfuric acid, do not react with the latter and have a boiling point of 40° to about 150° C. at 98 kPa, for example by means of highly fluorinated or perfluorinated, saturated aliphatic hydrocarbons, ethers or chlorofluorohydrocarbons, such as perfluoro-n-hexane; perfluorocyclohexane; perfluoro-n-heptane; perfluorohexyl methyl ether; perfluorodi-n-butyl ether; and trichlorotrifluoroethane.

If long-chain 1-iodoperfluoroalkanes (1-iodoperfluorodecane and upwards) are employed, the reaction mixture can contain solid constituents. In this case it is best to add, before the phase separation, at least one solvent which has the properties mentioned above, for example 1,1,2-trichlorotrifluoroethane.

The two liquid phases formed after cooling are separated from one another by customary methods, for example by decantation or by means of a separating funnel.

The lighter phase is vigorously mixed, for example by shaking or stirring, with 0.3 to 6% of its weight of water or with a corresponding quantity of an aqueous liquid. A mixture of sulfuric acid and water is preferably used as the aqueous liquid. If a solvent has been added, as described above, to the reaction mixture and/or to the lighter phase which has been separated off, the weight of the solvent should be deducted from the weight of the lighter phase in determining the quantity of water to be added.

In a preferred embodiment, the content of perfluorocarboxylic acid fluoride in the lighter phase which has been separated off is determined by analysis, for example by mixing a sample with water and determining the fluoride ions formed, using an ion-sensitive electrode or by means of the $^{19}F$ nuclear magnetic resonance spectrum. The quantity of water stoichiometrically required to decompose the acid fluoride is determined on the basis of the value found, and 105 to 130% of this quantity of water is mixed into the lighter phase, as described above.

It is also advantageous to warm the mixture of the lighter phase and water or an aqueous liquid to 40° to 100° C., particularly if perfluorocarboxylic acids having 8 or more C atoms are prepared. The effect of the warming is to accelerate and complete the decomposition of the acid fluoride. The organic, fluorinated solvent which may be present can be removed by evaporation before or after the hydrolysis. The pure perfluorocarboxylic acid is finally obtained by fractional distillation of the reaction product of the lighter phase with water, distillation being carried out at a pressure of 0.1 to 100 kPa, depending on the chain length of the perfluorocarboxylic acid formed.

Because of the moist hydrogen fluoride formed in the reaction of the lighter phase with water, the hydrolysis apparatus and the distillation column must be composed of a corrosion-resistant material or must be lined with the latter. Examples of such materials are fluorine-containing polymers of copolymers, for example polytetrafluoroethylene, polyvinylidene fluoride or tetrafluoroethylene/ethylene copolymers and also noble metals, such as tantalum or platinum.

It has been found that the fuming sulfuric acid obtained from the reaction with 1-iodoperfluoroalkane and separated off as the heavier phase cannot be simply reused by replacing the sulfur trioxide consumed and filtering, as described in German Pat. No. 1,211,619. The dissolved inorganic reaction products soon reach an unacceptably high level. Even after being used once, fuming sulfuric acid of this type has a corrosive effect on metals, and the iodine formed during the reaction is then only obtained in a very incomplete manner. However, it is desirable to recover the iodine present in a dissolved form as quantitatively as possible in the form of elementary iodine, since it is required as such for the preparation of the iodoperfluoroalkane starting compounds.

If the spent fuming sulfuric acid is heated in vacuo, sulfur trioxide and fluorosulfonic acid are obtained as volatile constituents, but only a little iodine. If precharged water or dilute sulfuric acid is allowed to react with the fuming sulfuric acid while cooling, the temperature remaining under 50° C., the precipitation of iodine is incomplete, even if the mixture is subsequently treated with strong oxidizing agents, such as chlorine or hydrogen peroxide.

Surprisingly, however, it has been found that the dissolved iodine is precipitated as elementary iodine in a very good yield if the fuming sulfuric acid separated off from the reaction mixture as the heavier phase is mixed, if appropriate while additionally warming, with 0.7 to 1.5 moles of water, or with a corresponding amount of an aqueous liquid, for example aqueous sulfuric acid, per mole of sulfur trioxide employed.

If less than 0.7 mole of water per mole of sulfur trioxide is used, the yield of elementary iodine precipitated is impaired. At more than 1.5 moles of water per mole of sulfur trioxide, the fuming sulfuric acid is diluted unnecessarily. Its re-use becomes less cost efficient, since larger quantities of sulfur trioxide are used in order to obtain a fuming sulfuric acid which is suitable for the reaction with 1-iodoperfluoroalkane. Preferably, 0.9 to 1.2 moles of water or aqueous liquid are used per mole of sulfur trioxide.

If water or a liquid containing a considerable amount of water, for example dilute sulfuric acid, is used, these liquids are preferably initially taken and the heavier phase which has been separated off is added, while agitating the mixture by stirring or shaking. If sulfuric acid of a higher concentration, for example 70 to 80% strength by weight sulfuric acid, is used as the aqueous liquid, the latter can be added slowly to the heavier phase which has been separated off, while agitating the mixture.

While the water is being added, the mixture warms up. The temperature of the mixture should reach at least 50° C. in order to obtain a good yield of precipitated elementary iodine. It is advantageous to adjust the temperature of the reaction mixture to 70° to 100° C., if necessary by additional warming or cooling. Above 100° C. an undesirable evaporation of the precipitated iodine takes place to an increasing extent.

When the water or the aqueous liquid is added, gaseous sulfur dioxide escapes from the mixture, and in the form of hydrogen fluoride, a large part of the fluorine which was present in the heavier liquid phase, separated off as described above. The gases evolved are preferably removed from the exit gas by being passed into milk of lime.

After the completion of the reaction with water, which lasts about 10 minutes to 1½ hours, depending on the quantity of water and the temperature selected, the mixture is cooled to 0° to +30° C. Above +30° C., the precipitation of iodine is less complete and the iodine is more difficult to filter off. The lower temperature limit of cooling is given by the fact that it is necessary to prevent, to a large extent, sulfuric acid or its hydrates from crystallizing out.

Elementary, solid iodine separates out virtually quantitatively from the cooled mixture. It is separated from the liquid phase by customary methods, for example by filtration or centrifuging, and is preferably washed, first with aqueous sulfuric acid within the concentration range of 80 to 30% by weight of $H_2SO_4$, and then with pure water. The iodine thus obtained can then be dried by known processes and can be purified, for example by distillation or sublimation.

It is advantageous to add, to the liquid phase remaining after the removal of the iodine, sulfur trioxide or fuming sulfuric acid having a high content of sulfur trioxide, preferably 50 to 70% by weight, in such a quantity that the whole mixture has a content of 15 to 45% by weight of sulfur trioxide. This mixture is used for the reaction of further 1-iodoperfluoroalkane.

In principle, it is also possible first to add water or aqueous liquids, for example aqueous sulfuric acid, to the reaction mixture consisting of 1-iodoperfluoroalkane and fuming sulfuric acid, and only then to separate from one another the two liquid phases which have been formed, but in this case difficulties can occur as a result of the precipitation of solids, which make the separation of the two liquid phases more difficult. Although these difficulties can be reduced by adding an inert solvent, for example the solvent mentioned earlier in the text on page 7, paragraph 4, this general addition of solvent makes the process more expensive without removing the difficulties in a satisfactory manner.

The new process described in the preceding pages can be carried out particularly advantageously in the reaction, with fuming sulfuric acid, of 1-iodoperfluoro-n-octane or mixtures of various 1-iodoperfluoroalkyl compounds containing a predominant fraction of compounds having 6 to 14 C atoms and at least 25% by weight of 1-iodoperfluoro-n-octane.

The process according to the invention makes it possible to obtain, in high yields and in a high purity, in particular, straight-chain perfluorocarboxylic acids and, especially, perfluorooctanoic acid, which is of importance in industry, and also elementary iodine. It also makes it possible to recover and recycle the sulfuric acid, and the reaction of the fuming sulfuric acid with the 1-iodoperfluoroalkane can be carried out in steel vessels without fairly severe corrosion.

The following examples are intended to illustrate the process according to the invention in greater detail.

EXAMPLE 1

Preparation of perfluorooctanoic acid:

A 2 l stirred autoclave made of V2A steel is flushed with $N_2$ and is then charged with 900 g of 1-iodoperfluoro-n-octane ($n$—$C_8F_{17}I$, 1.648 moles) and 1,700 g of fuming sulfuric acid containing 35% by weight (=7.44 moles) of free sulfur trioxide (876 ml of 35% strength oleum) and is closed. The molar ratio of sulfur trioxide to 1-iodoperfluoroalkane is 4.5:1. The mixture is heated to 155° C. in the course of 90 minutes, is stirred for 4 hours at this temperature and is then cooled to room temperature. The autoclave is discharged into a separating funnel, and the phases which have formed are separated after standing for one hour. 1,900 g of dark brown, spent fuming sulfuric acid are obtained as the lower, heavier phase. The upper, lighter, pale pink phase comprises 670 g of a mixture of fluorine compounds which, according to its $^{19}F$ nuclear magnetic resonance spectrum, is composed of 48 mole % of $n$—$C_7F_{15}COF$ and 48 mole % of $n$—$C_7F_{15}COOH$ and of unreacted $n$—$C_8F_{17}I$ (approx. 3 mole %).

15 g of water (=2.2% of the weight of the lighter phase) are added to the lighter phase at 60° C. in an apparatus lined with polyvinylidene fluoride sheet and equipped with a polytetrafluoroethylene stirrer, and the mixture is stirred vigorously. The gas containing hydrogen fluoride which is evolved is passed into a suspension of calcium hydroxide. The gas evolution is complete after 30 minutes. The crude product thus obtained is fractionally distilled at 5.3 kPa. This gives 20 g of first runnings up to a boiling point of 113° C., composed essentially of 1-iodoperfluoro-n-octane, and 648 g of colorless, pure perfluorooctan-1-oic acid (boiling point 113° C./5.3 kPa, melting point 54° to 55° C.). The yield is 98%, relative to $n$—$C_8F_{17}I$ which has reacted.

770 g of 80% strength by weight sulfuric acid are added dropwise, in the course of 30 minutes and while stirring vigorously in a stirred apparatus, to the heavier phase which has been separated off. This sulfuric acid contains 154 g (=8.55 moles) of water. 1.15 moles of water are used per mole of the sulfur trioxide originally employed. The temperature is adjusted to 85° C. The gases evolved (sulfur dioxide and hydrogen fluoride) are neutralized with milk of lime. The mixture is cooled to 20° C. and the finely crystalline iodine which has precipitated is separated from the sulfuric acid with the aid of a glass filter and is washed successively with 200 ml of 80% strength by weight $H_2SO_2$, then with 200 ml of 50% strength by weight $H_2SO_4$ and finally with 500 ml of $H_2O$. 209 g of moist iodine (water content 4% by weight) are obtained, corresponding to a recovery of 99%, relative to the $n$—$C_8F_{17}I$ which has reacted.

EXAMPLES 2 TO 9

Table 1 shows the results of smaller batches which are obtained using fuming sulfuric acid containing 35% by weight of sulfur trioxide, with variations in the $SO_3$: $n$—$C_8F_{17}I$ molar ratio and reaction time. Working up is effected analogously to Example 1.

It will be seen from Examples 8 and 9 that, although a high sulfur trioxide: $n$—$C_8F_{17}I$ molar ratio leads to high degrees of conversion, nevertheless the yield of carboxylic acid is reduced markedly by the formation of by-products ($C_8F_{17}H$, $C_6F_{13}CF=CF_2$ and $C_6F_{13}CO_2H$).

which are combined with the lighter phase. According to the $^{19}F$ nuclear magnetic resonance spectrum, the latter contains 5 mole % of $n$—$C_6F_{13}I$, 43 mole % of $n$—$C_5F_{11}COF$ and 47 mole % of $n$—$C_5F_{11}CO_2H$, the remainder being unknown compounds (probably $n$—$C_6F_{13}OSO_2F$). The lighter phase is vigorously mixed at 20° C. with 2.8 g of water (=4% of the weight of the lighter phase). After the gas evolution is complete, fractional distillation at normal pressure gives 7.5 g of first runnings and 60.6 g of pure perfluorohexan-1-oic acid (boiling point 152° to 153° C., yield 81%, relative to $n$—$C_6F_{13}I$ which has reacted).

35 g of 50% strength by weight sulfuric acid are added, in the course of 20 minutes and while stirring vigorously, to the heavier phase which has been separated off and extracted as described above. This sulfuric acid contains 17.5 g (=0.97 mole) of water. 0.85 mole of water is used per mole of sulfur trioxide originally employed. The temperature is adjusted to 95° C. by warm-

TABLE 1

The results of reacting n-$C_8F_{17}I$ with fuming sulfuric acid containing 35% by weight of sulfur trioxide at 155° C.*

| Example No. | Quantities employed | | $SO_3$/n-$C_8F_{17}I$ molar ratio | Duration of reaction (hours) | Conversion (%) | Yield of n-$C_7F_{15}CO_2H$ (%) |
|---|---|---|---|---|---|---|
| | n-$C_8F_{17}I$ (g) | Sulfuric acid + $SO_3$ (g) | | | | |
| 2 | 100 | 95 | 2.27 | 4 | 47 | 38 |
| 3 | 100 | 142 | 3.39 | 4 | 72 | 63 |
| 4 | 100 | 142 | 3.39 | 6 | 78 | 70 |
| 5 | 100 | 142 | 3.39 | 8 | 83 | 75 |
| 6 | 100 | 190 | 4.54 | 4 | 91 | 82 |
| 7 | 100 | 190 | 4.54 | 6 | 96 | 87 |
| 8 | 100 | 390 | 9.32 | 4 | 96 | 78 |
| 9 | 100 | 600 | 14.33 | 4 | 98 | 72 |

*Carried out in a V4A shaking autoclave. The heating-up and cooling-down times were each 1 hour. The yields of perfluorooctanoic acid (distilled acid) relate to the n-$C_8F_{17}I$ employed.

EXAMPLE 10

Re-use of the concentrated sulfuric acid produced in the recovery of iodine:

700 g of sulfur trioxide are dissolved in 1,005 g of the sulfuric acid obtained in accordance with Example 1 after the removal of iodine. The 1,705 g of fuming sulfuric acid formed in this manner, containing about 35% by weight of sulfur trioxide, are reacted with 900 g of $n$—$C_8F_{17}I$ as in Example 1. The yields, relative to $n$—$C_8F_{17}I$ converted, are 645.6 g of $n$—$C_7F_{15}CO_2H$ (97.5%) and 210.2 g of moist iodine ($H_2O$ content 4.7%, yield 98.7%).

140 g of water are added to a further 630 g of the end product sulfuric acid obtained in accordance with Example 1. These 770 g of 80% strength by weight sulfuric acid are re-used in accordance with Example 1.

EXAMPLE 11

Perfluorohexanoic acid 111.5 g (=0.25 mole) of 1-iodoperfluoro-n-hexane ($n$—$C_6F_{13}I$) and 260 g of fuming sulfuric acid containing 35% by weight of sulfur trioxide (=1.14 moles) are heated to 155° C. in the course of 90 minutes in a shaking autoclave and are shaken at this temperature for 3.5 hours. The molar ratio of sulfur trioxide to 1-iodoperfluoroalkane is 4.6:1. After the autoclave has been cooled, the phases are separated. This gives 70.3 g of lighter phase and 283.9 g of heavier phase. After extracting the heavier phase with three times 40 ml of 1,1,2-trichloro-trifluoroethane and evaporating off the extraction agent, 5.5 g of liquid residue are obtained, ing. The gases evolved are neutralized with milk of lime.

The mixture is cooled to 12° C. and the iodine which has precipitated is filtered off and washed as described in Example 1. 30 g of moist iodine (water content 4% by weight) are obtained, corresponding to a recovery of 95.5%, relative to the $n$—$C_6F_{13}I$ which has reacted.

EXAMPLE 12

Perfluorodecanoic acid 129.2 g of 1-iodoperfluoro-n-decane ($n$—$C_{10}F_{21}I$, 0.2 mole) and 207.7 g of fuming sulfuric acid containing 35% by weight of sulfur trioxide (=0.91 mole) are shaken for 8 hours at 155° C. in a steel autoclave. The molar ratio of sulfur trioxide to 1-iodoperfluoroalkane is 1:4.6. After cooling to room temperature, 50 ml (=78.8 g) of 1,1,2-trichlorotrifluoroethane are added, the mixture is again shaken vigorously and the phases are separated. 186 g of the lighter phase are obtained. According to the $^{19}F$ nuclear magnetic resonance spectrum, this phase contains, besides the solvent, 62 mole % of $n$—$C_9F_{19}COF$, 21 mole % of $n$—$C_9F_{19}CO_2H$ and 17 mole % of $n$—$C_{10}F_{21}I$. 2.5 g of $H_2O$ (=2.3% of the weight of the lighter phase less the solvent) are added to this phase and the mixture is heated under reflux at approx. 55° C. for 20 minutes. After distilling off the solvent, 25 g of first runnings (boiling point 103° to 149° C./9.3 kPa) and 72.9 g of main fraction (boiling point 149° to 153° C./9.3 kPa) are obtained by fractional distillation. Neglecting the quantity of acid present in the first runnings, the yield of n-perfluorodecanoic acid is 85.1%, relative to the 83% conversion of $n$—$C_{10}F_{21}I$.

The heavier phase which has been separated off is added to 24 g (=1.33 moles) of water, while stirring vigorously. 1.47 moles of water are used per mole of sulfur trioxide employed originally. The temperature is adjusted to 73° C. The gases evolved are neutralized with milk of lime.

The mixture is cooled to 8° C., and the iodine which has precipitated is filtered off and washed as described in Example 1. 21.2 g of moist iodine (water content 4% by weight) are obtained, corresponding to a recovery of 96.5%, relative to the $n$—$C_{10}F_{19}I$ which has reacted.

EXAMPLE 13

Preparation of a mixture of perfluorocarboxylic acids 115.3 g (0.22 mole) of a mixture of 1-iodoperfluoroalkanes, composed of 43.5% of $n$—$C_6F_{13}I$, 33.0% of $n$—$C_8F_{17}I$, 16.5% of $n$—$C_{10}F_{21}I$ and 7.0% of $n$—$C_{12}F_{15}I$, are reacted with 228 g of fuming sulfuric acid containing 35% by weight of sulfur trioxide (=1 mole) for 6 hours at 155° C. in a shaking autoclave. The molar ratio of sulfur trioxide to 1-iodoperfluoroalkane is 4.5:1.

After cooling and separating the phases, 93.2 g of a lighter phase are obtained which has the following composition: 26 mole % of perfluoroalkanoic acid fluorides, 63.0 mole % of perfluoroalkan-1-oic acids, 6.5 mole % of unreacted 1-iodoperfluoroalkanes and 4.5 mole % of compounds of the formula $R_fOSO_2F$. Mixing the lighter phase with 3 g (=3.2% of the weight of this phase) of water at an initial temperature of 20° C. and a final temperature of 80° C., and subsequent distillation gives 7 g of first runnings (boiling point 80° to 149° C.) and 66.8 g of a main fraction which passes over between 113° C./13.3 kPa and 145° C./6.7 kPa. The yield of mixed $C_6$ to $C_{12}$ perfluoroalkanecarboxylic acids, relative to a 93.5% conversion, is 82.8%.

The recovery of iodine from the heavier phase, which is carried out analogously to Example 1, gives a 97.2% yield of iodine, relative to iodoperfluoroalkane which has reacted.

We claim:

1. In the process for the preparation of pure, saturated perfluoroalkane-1-carboxylic acids having 6 to 14 C atoms from the corresponding 1-iodoperfluoroalkanes, by reacting the 1-iodoperfluoroalkanes with fuming sulfuric acid containing 15 to 45 percent by weight, relative to the solution, of dissolved sulfur trioxide, at temperatures of 100° to 180° C., the molar ratio of sulfur trioxide to 1-iodoperfluoroalkane being 2:1 to 15:1, the resulting two liquid phases being separated from one another when the reaction is complete and the separated lighter liquid phase being distilled, the improvement which comprises mixing, at room temperature or elevated temperature, the lighter liquid phase with 0.3 to 6 percent of its weight of water or with a corresponding amount of an aqueous liquid, and then distilling this mixture at a pressure of 0.1 to 100 kPa, and also mixing the heavier liquid phase, which has been separated off after the reaction with fuming sulfuric acid, with 0.7 to 1.5 moles of water, or with a corresponding amount of an aqueous sulfuric acid, per mole of sulfur trioxide employed, then cooling to 0° to 30° C., filtering off the solid iodine which has been precipitated, washing it with aqueous sulfuric acid and with water.

2. A process as claimed in claim 1, wherein sufficient sulfur trioxide is added to the concentrated sulfuric acid produced after the removal of the iodine to give a solution containing 15 to 45% by weight of sulfur trioxide, and this solution is used for reacting with further 1-iodoperfluoroalkane.

3. A process as claimed in either of claim 1 or 2, wherein the lighter liquid phase which has been separated off is warmed to 40° to 100° C. after water has been added to it.

4. A process as claimed in claim 1 or 2, wherein the temperature of the heavier liquid phase which has been separated off and to which water has been added is adjusted to 70° to 100° C.

5. A process as claimed in claim 1 or 2, wherein 1-iodoperfluoro-n-octane or mixtures of 1-iodoperfluoroalkyl compounds containing a proportion, relative to the mixture, of at least 25% by weight of 1-iodoperfluoro-n-octane, are reacted with fuming sulfuric acid.

6. A process as claimed in claim 1 or 2, wherein the molar ratio of sulfur trioxide to 1-iodoperfluoroalkane in the reaction of 1-iodoperfluoroalkane with fuming sulfuric acid is 3:1 to 6:1.

7. A process for recovering a substantially pure, saturated perfluoroalkane-1-carboxylic acid having 6 to 14 C atoms, and for recovering byproduct iodine, from a reaction mixture resulting from the reaction of the corresponding 1-iodoperfluoroalkane with fuming sulfuric acid containing 15-45% by weight, relative to the solution of dissolved sulfur trioxide, said reaction mixture comprising a lighter liquid phase and a heavier liquid phase containing sulfuric acid and iodine, said process comprising:

separating said lighter liquid phase from said heavier liquid phase;

mixing with the separated lighter liquid phase 0.3 to 6 percent, based upon the weight of the lighter liquid phase, of water or an aqueous liquid, then distilling the resulting mixture at a pressure of 0.1 to 100 KPa;

mixing with the separated heavier liquid phase 0.7 to 1.5 moles of water or sulfuric acid per mole of sulfur trioxide employed in said reaction and then cooling the resulting mixture to 0° to 30° C. to precipitate as a solid the iodine contained in the heavier liquid phase; filtering off the thus-precipitated solid iodine; and washing the precipitated solid iodine with sulfuric acid and with water.

* * * * *